United States Patent [19]
Hopf

[11] Patent Number: 5,814,046
[45] Date of Patent: Sep. 29, 1998

[54] PEDICULAR SCREW AND POSTERIOR SPINAL INSTRUMENTATION

[75] Inventor: Christoph Hopf, Mainz, Germany

[73] Assignee: Sofamor S.N.C., Rang Du Fliers, France

[21] Appl. No.: 436,192

[22] PCT Filed: Nov. 12, 1993

[86] PCT No.: PCT/US93/10966

§ 371 Date: May 10, 1995

§ 102(e) Date: May 10, 1995

[87] PCT Pub. No.: WO94/10928

PCT Pub. Date: May 26, 1994

[30] Foreign Application Priority Data

Nov. 13, 1992 [FR] France ................................. 9213694

[51] Int. Cl.$^6$ .................................................. A61B 17/56
[52] U.S. Cl. ............................... 606/61; 606/72; 606/73; 81/443
[58] Field of Search ............................ 81/443, 444, 445, 81/442, 453, 455, 125, 457, 124.2; 606/72, 73, 61

[56] References Cited

U.S. PATENT DOCUMENTS

| | | | |
|---|---|---|---|
| 2,532,972 | 12/1950 | Vertin | 81/443 |
| 2,634,641 | 4/1953 | Hodges | 81/125 |
| 3,068,922 | 12/1962 | Hill | 81/457 |
| 3,377,894 | 4/1968 | Johnson | 81/125 |
| 3,604,487 | 9/1971 | Gilbert | 145/50 D |
| 4,393,583 | 7/1983 | Zwald | 81/124.2 |
| 4,648,388 | 3/1987 | Steffee | 128/69 |
| 4,877,020 | 10/1989 | Vich | 81/443 |
| 5,024,213 | 6/1991 | Asher et al. | 606/61 |
| 5,030,220 | 7/1991 | Howland | 606/61 |
| 5,129,900 | 7/1992 | Asher et al. | 606/61 |
| 5,147,363 | 9/1992 | Harle | 606/73 |
| 5,507,211 | 4/1996 | Wagner | 81/125 |
| 5,520,688 | 5/1996 | Lin | 606/73 |
| 5,545,163 | 8/1996 | Miller et al. | 606/61 |

Primary Examiner—Michael Buiz
Assistant Examiner—Julian W. Woo
Attorney, Agent, or Firm—Woodard, Emhardt, Naughton Moriarty & McNett

[57] ABSTRACT

The instrumentation comprises for each lumbar vertebra two pedicular screws having two screw threads, one of the screw threads corresponding to the region of penetration of the screw in the pedicle, two rods having asperities respectively associated with a pedicular screw and secured to the latter by connection elements provided with elements for clamping the rods. Each connection element is in one piece and the screw thread corresponding to the region of penetration of the screw in the pedicle terminates in an annular shoulder against which the connection element bears which is separated by a smooth part from the screw thread outside the region of penetration in the pedicle. This instrumentation permits both returning the slipped vertebrae rearwardly and pivoting it in the desired direction of rotation, it being possible to carry out the derotation action slowly and by controlling the movement so that the surgeon achieves on the whole in the two movements an excellent precision in the repositioning of vertebrae relative to the neighboring vertebrae.

5 Claims, 6 Drawing Sheets

PEDICULAR SCREW AND POSTERIOR SPINAL INSTRUMENTATION

The invention relates to lumbar osteosynthesis instrumentation for the correction of spondylolisthesis.

It is known that, substantially, spondylolisthesis is the forward displacement of a vertebra relative to its lower neighbour. In theory, any vertebra may be affected, but the fifth and the fourth lumbar vertebrae are the most commonly concerned.

Affecting more frequently women or young girls than men, spondylolisthesis is usually classified into five types: dysplastic, isthmian, traumatic, degenerative and pathological.

Its degree of seriousness is measured by the distance travelled through by the displaced vertebra with respect to its lower neighbour.

There are four stages:

The first stage is a displacement of a quarter of the antero-posterior diameter of the vertebral body.

The fourth stage corresponds to a complete displacement of the vertebral body.

The second and third stages are the intermediate stages.

Heretofore, although there are certain surgical techniques for the treatment of spondylolisthesis, either by the direct traction on the slipped vertebra, or by the screwing of the pedicles of this slipped vertebra, the reduction of the spondylolisthesis is not always satisfactory, above all in the cases of serious spondylolisthesis.

Surgery is indeed indicated for those who have a long past of lumbalgia or sciatica, in the case of evidence of a vertebral canal stenosis, a compression of the cauda equina or a subjacent motor lesion, or those whose spondylolisthesis rapidly evolves toward stage 3 or stage 4.

Generally, in surgery, an anterior or posterior vertebral fusion, laminectomy with decompression of the posterior structures and an excision of the hypertrophied mass of the fibrous tissue in the region of the lysis may be indicated.

In isthmian spondylolisthesis, the bilateral isthmian lyses are liable to be associated with a considerable pseudoarthrosis in relation with an emerging nerve root. The discal state in the region of the spondylolisthesis sometimes requires a radiculographic or discographic assessment. In vertebral canal stenoses, the decompression without fusion may be a surgical operation.

In actual fact, an effective orthopedic surgery consists in returning the vertebra not only onto the axis of the spine but also to a position which is as correct as possible relative to the neighbouring vertebrae. Over a period of time, or in the course of its displacement, this vertebra in fact might have been subjected to lateral thrusts which have caused it to pivot horizontally to a more or less large extent so that a correct repositioning of the vertebra of course implies its rearward return but also a derotation.

Attempts have already been made to correct spondylolisthesis, for example by means of devices consisting of two pedicular screws interconnected by a transverse plate which, by screwing a nut bearing against the plate, act solely by translation of the concerned vertebra for putting it into alignment with the neighbouring vertebrae.

Thus, the device disclosed in French patent 2 615 095 (87 06 864) employs two rods which are longitudinally fixed in the vertebral column with the aid of pedicular screws and each serve as support means for two screws having a double screw thread connected to the vertebra to be corrected. These two double thread screws are transversely connected by a rigid plate constituting a bipedicular base. It is this transverse plate which permits acting on the vertebra to be corrected owing to the provision of a median opening for receiving traction forceps.

In fact, such a device does not permit acting in a sufficiently satisfactory manner, and experience has shown that a traction on the median part of the plate has for effect to rearwardly return the vertebra to be corrected too rapidly. Further, if this vertebra must be derotated, it has been found that the presence of the plate is liable to prevent the required derotation action owing to the fact that this induces at the same time a certain return of the vertebra.

Now, surgical experience has revealed that it is desirable to act slowly on the vertebra by acting on each one of the double thread screws independently, so that the surgeon can gradually adjust for each particular case his vertebra derotation and/or return action.

Moreover, such a device is relatively complex and costly owing to the number of its component parts which further increases the mounting difficulties encountered by the surgeon during the surgical operation. As concerns in particular the double thread screw, in addition to the fact that it is long and costly to produce, its implantation in the pedicles is not at all convenient.

Further, this double thread screw is subjected to extremely high shear stresses, mainly in the region of the junction with the instrumentation appliances or in the upper part of the screw thread.

An object of the invention is to provide a lumbar osteosynthesis instrumentation for the correction of spondylolisthesis, which permits both returning the vertebra to the rear and pivoting it in the desired direction of rotation. Another object of the invention is to provide a double thread pedicular screw so arranged as to overcome the aforementioned drawbacks while permitting mass production which is cheaper than in the case of screws known in the art which can only be produced on a small scale.

The osteosynthesis instrumentation according to the invention comprises, for each lumbar vertebra, two pedicular double thread screws, one thread of which corresponds to the region of penetration of the screw in the pedicle, two rods having surface asperities respectively associated with a pedicular screw and connected to the latter by connection elements provided with elements for clamping the rods.

According to the invention, each connection element is in one piece and the screw thread corresponding to the region of penetration of the screw in the pedicle terminates on an annular shoulder on which the connection element bears.

The derotation action exerted by means of this instrumentation has the advantage that it can be carried out slowly and with a certain amount of control over the movements, thereby affording on the whole in the two movements an excellent precision in the repositioning of the vertebra relative to its neighbouring vertebrae.

Further, the arrangement of a transverse shoulder into which tangentially fades the screw thread of the part of the screw serving to penetrate the pedicle, provides a reinforcement or strengthening resisting the shear stresses in this region. The continuous peripheral shoulder may also act as a support for an added part.

According to a particular feature of the invention, the end of the screw thread outside the part of the screw serving to penetrate the pedicle is extended by a screw threaded rod adapted to cooperate with an ancillary screwing device.

The instrumentation according to the invention comprises an ancillary device for screwing the pedicular double thread screw, this device bearing against the screw threaded extension of said screw. This ancillary device comprises a rod provided with an end grip and includes a tubular end part which is arranged to permit the insertion of the operating part of the double thread screw, has a conical free end part remote from the grip tapering toward the grip and is provided with at least one longitudinal slot. This ancillary device further comprises a tube freely slidable on the rod for the purpose of surrounding and gripping the conical end part of its tubular end part for the purpose of clamping it on the operating part of the pedicular screw.

With this ancillary device, the length of the operating screw thread is almost completely enclosed in the tubular end part and clamped owing to the action of the second tube when the latter surrounds the conical end part of the tubular end part. After having provided a prior bore in the pedicle, the surgeon can in this way easily screw the double thread screw in position.

Further features and advantages of the invention will be apparent from the following description with reference to the accompanying drawings which illustrate two embodiments of the invention by way of non-limitative examples.

Figure 1:
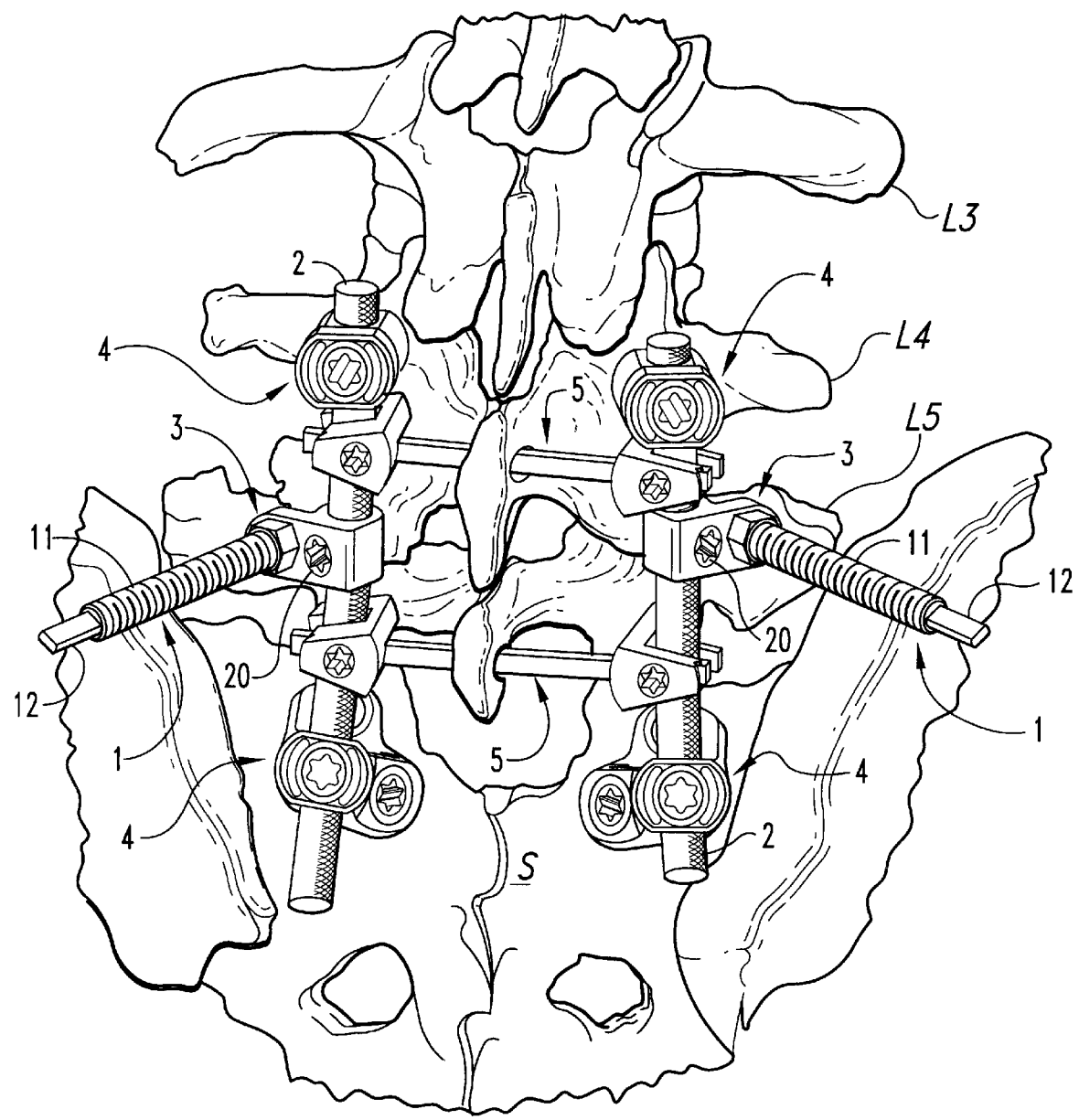
FIG. 1 is a perspective view from above of one embodiment of the lumbar osteosynthesis instrumentation according to the invention, mounted on the first lumbar vertebra and on the sacrum.
Figure 2:
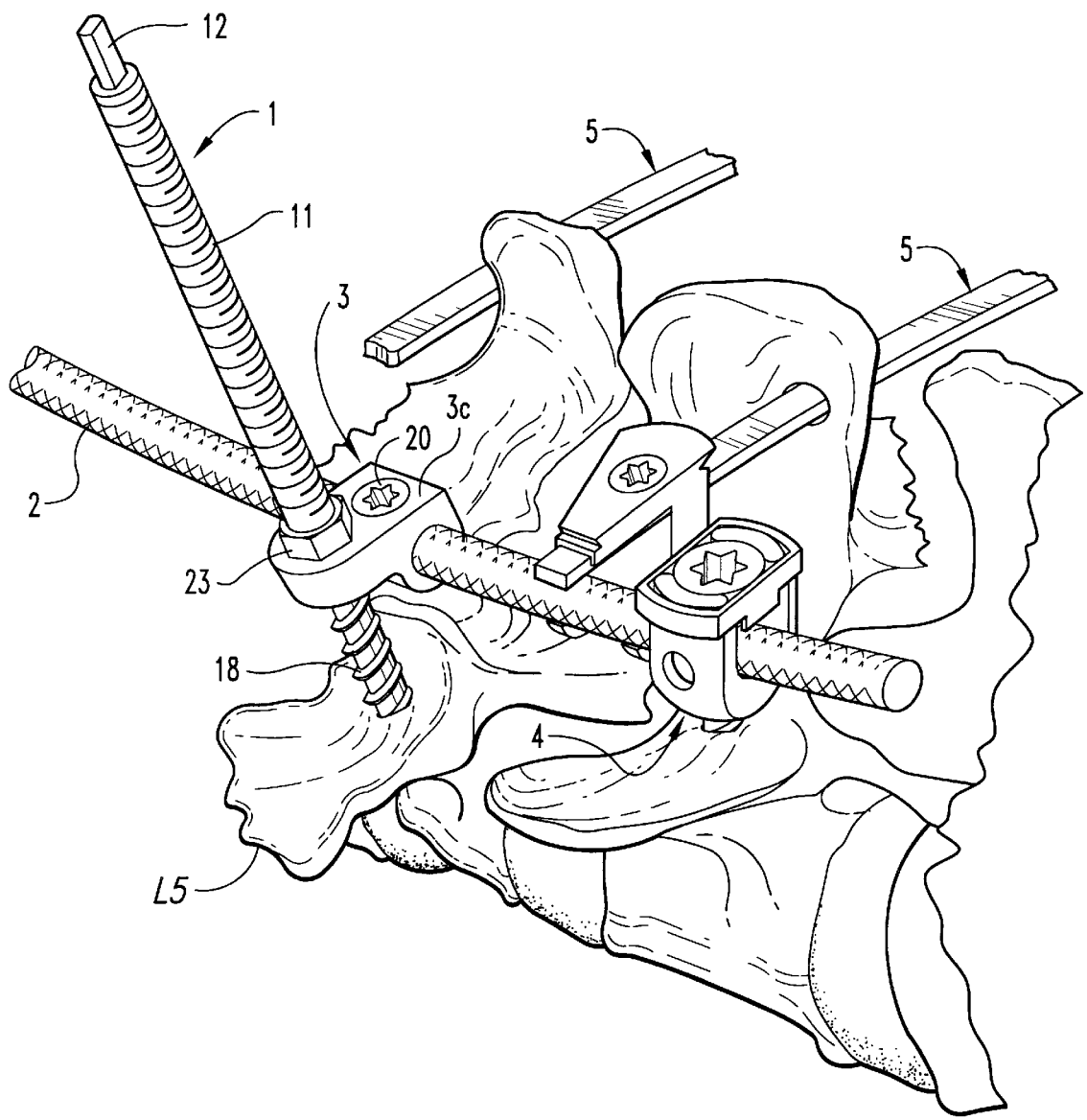
FIG. 2 is a partial perspective view of the instrumentation shown in FIG. 1.
Figure 3:
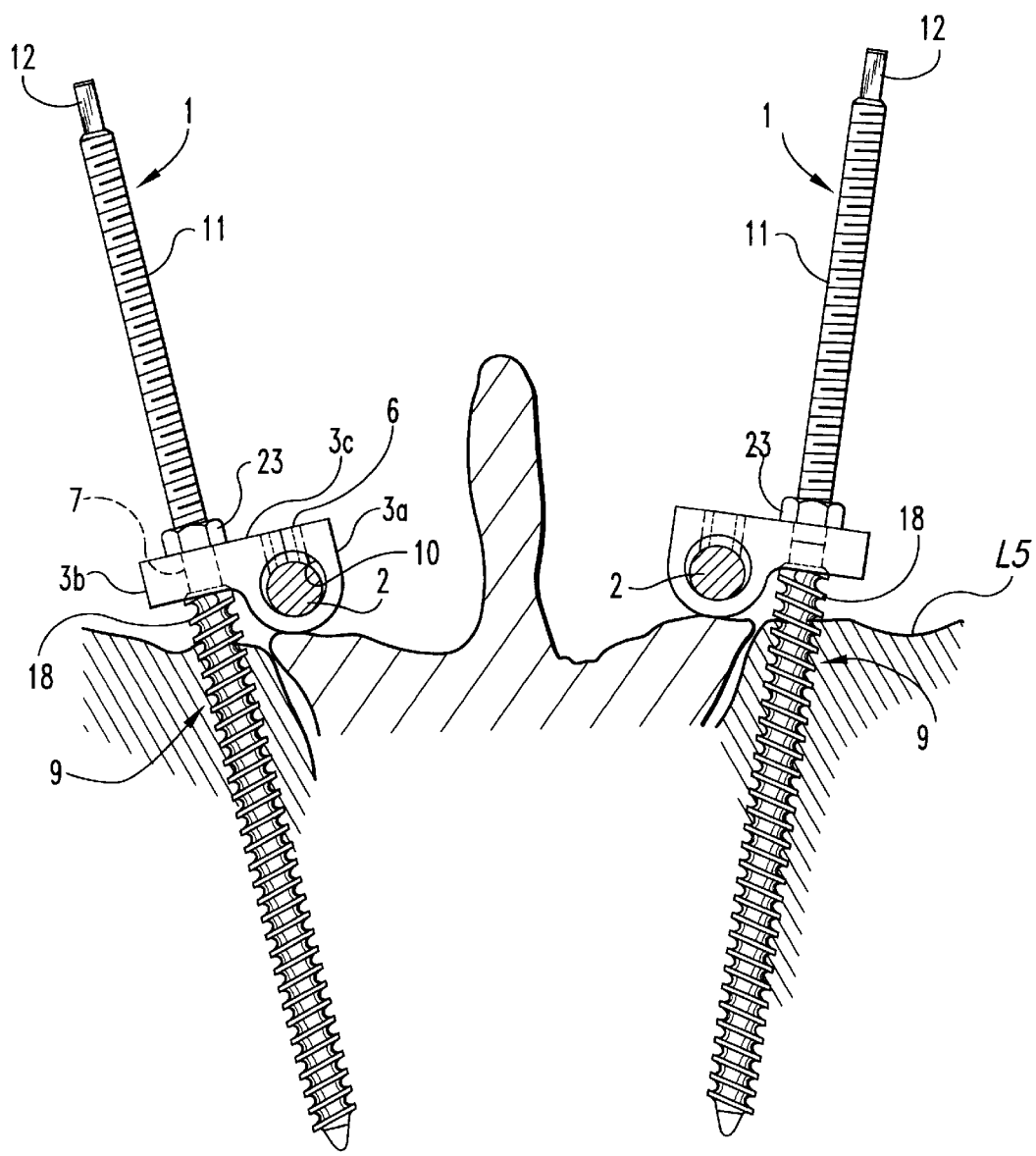
FIG. 3 is an elevational view in the transverse direction, partly in section, of the instrumentation shown in FIGS. 1 and 2.

The lumbar osteosynthesis instrumentation shown in FIGS. 1 to 3 is adapted to correct spondylolisthesis by the posterior approach.

It comprises, for each lumbar vertebra to be corrected, for example the vertebra L5, two pedicular screws 1 having two screw threads, two cylindrical rods 2, preferably two rods of the so-called Cotrel type having surface asperities or knurling extending longitudinally along the concerned lumbar segment (vertebrae L5, L4 and sacrum S in the assembly shown in FIG. 1), connection elements 3 connecting each pedicular screw 1 to the adjacent rod 2, pedicular screws 4 for securing the rods 2 to the vertebra L4 and to the sacrum S, and devices 5 providing a transverse connection between the rods. All these elements except the pedicular screws 1 and the connection elements 3 are known per se and therefore need no special description.

Figure 7:
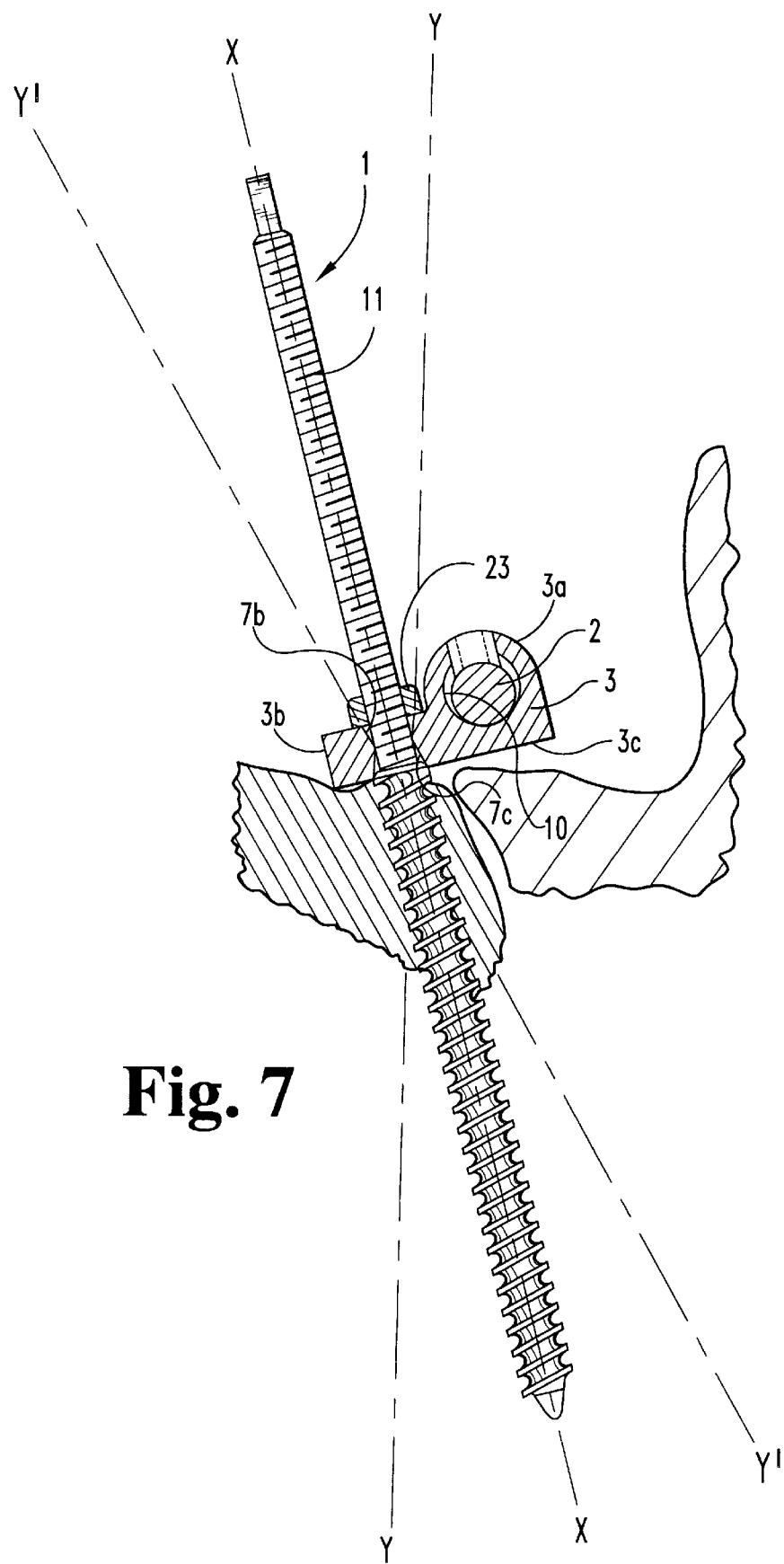
FIG. 7 is a sectional view taken on line 7—7 of FIG. 6.

Each connection element 3 has, when viewed in the transverse direction, a substantially L-shaped profile consisting of an enlarged base 3a in which is provided a through passage 10 receiving the rod 2 and having an axis X—X. This portion 3a has on one side a cylindrical surface and on the other side a planar surface and is extended by a thin portion 3b. The latter has two parallel planar surfaces and is provided with an opening 7 for the passage of the pedicular screw 1. The opening 7 consists of a cylindrical central part having an axis Z—Z extended on each side by two conical parts 7b, 7c opening onto the planar surfaces. The taper of these conical parts is such that it permits an inclination of the axis of the screw 11 relative to the axis Z—Z of about ±15°, the angular limits of this axis corresponding to the axes Y—Y and Y'—Y' (FIG. 7). A tapped opening 6 transversely opens onto the bore or passage 10 and receives a screw 20 for radially clamping the rod 2. The surface 3c of the element 3 remote from the passage 10 is completely planar.

The element 3 constitutes the means for securing the rod 2 and the means for screwing the screw 1. The distance between the axes of the screw 1 and rod 2 vary with the subject so that the surgeon can choose the most appropriate element 3.

Each screw 1 comprises from its point 8 a first screw threaded part 9 extending to the length of penetration of the screw 1 in the pedicular and a second screw threaded part 11 which is outside the region of penetration in the pedicle and is termed the "operating" part. On the side remote from the screw threaded part 9 the operating part 11 is extended by a profiled end portion 12, constituted for example by two flats 13 adapted to permit both the gripping of the double thread screw 1 and the screwing thereof by means of an ancillary device 14 (FIG. 5) which will be described hereinafter.

At the end remote from the profiled end portion 12, the screw threaded operating part 11 is extended by a short smooth region 15 terminating in a continuous peripheral shoulder 16 constituting the end of the screw threaded part 9. This shoulder 16 bears against the planar surface of the element 3 which is the most remote from the screw threaded part 11, consequently the screw 1 cannot pass through the element 3.

The screw thread 18 of this screw threaded part is adjacent the shoulder 16 and the depth of the thread 21 close to the shoulder 16 gradually diminishes until it tangentially merges with or fades onto a cylindrical sector 22 bordered by the shoulder 16 which thus forms a screw reinforcing region in this position. The shoulder 16 may act as a support for a device or an associated connection element 3.

The operating part 11 of the screw 1 is constituted by a metal screw thread of small pitch, for example between 0.5 and 2 mm and preferably between 0.8 and 1 mm, adapted to receive a nut 23 for clamping the connection element 3 against the shoulder 16.

This instrumentation has the following advantages:

The fact that the connection element 3 is made in a single piece not only makes this element cheaper to manufacture but also simplifies the positioning of the element by the surgeon, and above all improves the strength of the connection between the rod 2 having asperities and the pedicular screw 1.

As previously explained, the pedicular double thread screw 1 is subjected to high mechanical stresses of multiple origins; it must resist these various stresses for a relatively long period of time the duration of which depends on each patient. The screw 1 must therefore be as simple as possible to mount during the surgical operations, but must also have sufficient strength to withstand all the forces during and after the operation. Now, with the pedicular screws employed heretofore, it has been found that fractures generally occur in the region between the two screw threads. The invention remedies this situation by terminating the screw thread 18 for anchoring in the pedicle in the substantially tangential region 22. Consequently, the screw thread 18 does not "open out" onto the shoulder 16 for supporting the connection element 3 and consequently ensures that this shoulder 16 has a peripheral continuity and a sufficient supporting thickness. This supporting thickness thus affords the maximum mechanical resistance to the forces transmitted to the connection element 3 and therefore exerted by the latter.

Another advantage afforded by this arrangement of the anchoring screw thread 18 resides in the fact that, when it is desired to effect a bicortical anchorage by reaching the opposite cortical part of the vertebra and with the screw thread length corresponding to the length of the passage through the vertebra, the surgeon is informed of the desired final position of the screw thread. The stoppage of the latter in its upper part indeed constitutes a warning in that the surgeon must suddenly exert a higher torque. He must therefore stop his screwing effort.

Owing to the provision of the profiled end portion 12, the engagement of the pedicular screw 1 by the ancillary device 14 no longer occurs in the central region of the screw, as described in said patent 2 615 095, but at the free end of the screw. This end region may be in the form of two flats 13 provided on a smooth, or optionally screw threaded, end part to permit the ancillary device 14 to act on the screw.

This ancillary device comprises a rod 24 provided with a tubular end part 25 and, at its opposite end, a manual grip 26. The tubular part 25 is so dimensioned as to permit the insertion therein of the operating part 11 of the screw 1, and the ancillary device 14 is completed by a tube or sleeve 27 coaxial with the rod 24 and slidably mounted on the latter so as to be capable of surrounding the tubular part 25 at the end of its travel.

Figure 5:
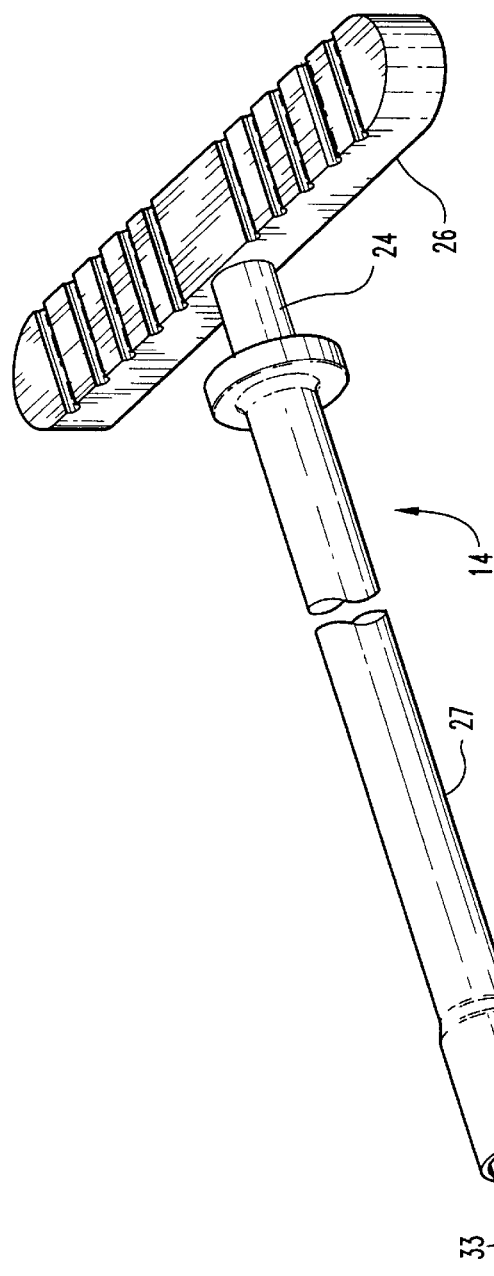
FIG. 5 is a perspective view of an embodiment of the ancillary device for mounting the pedicular screw shown in FIG. 4.
Figure 4:
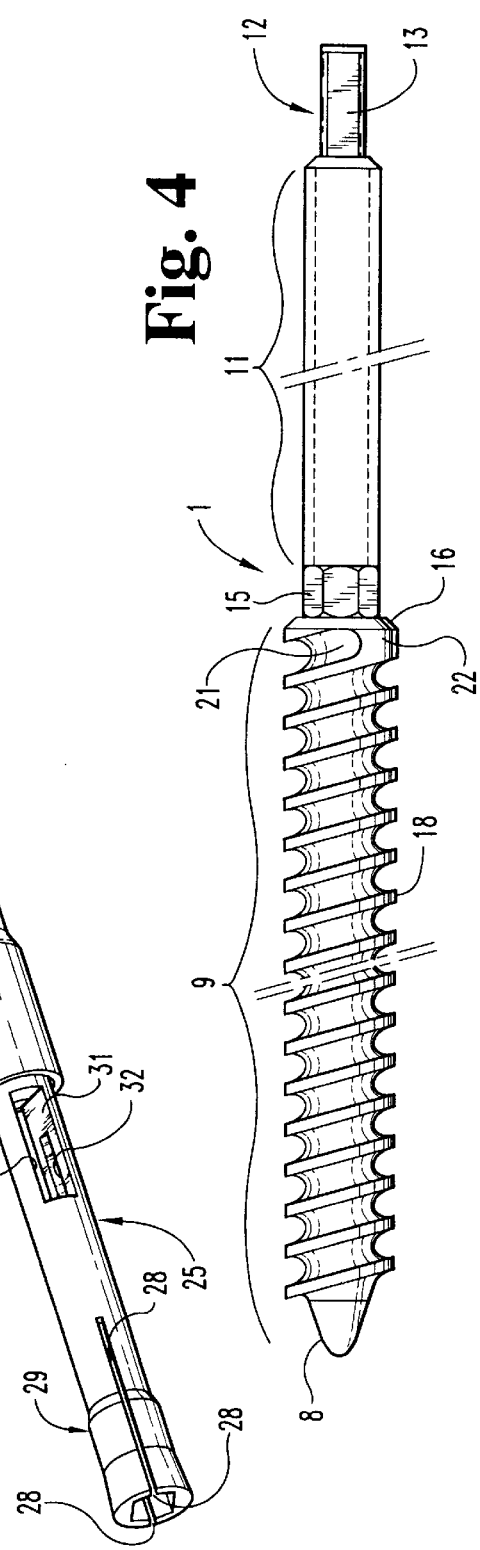
FIG. 4 is an elevational view to a larger scale of a pedicular double thread screw which is part of the instrumentation shown in FIGS. 1 to 3.

The tubular part 25 is provided with longitudinal slots 28 starting at its free end, for example three slots as illustrated, extending along a part of the length of the region 25. The free end portion 29 of the latter is conical and tapers in the direction toward the grip 26. Beyond the slots 28, at a certain distance from the latter, there is provided a hollow profile matching the profiled end portion 12 of the screw, for example, as shown in FIG. 5, two flats 31 whose longitudinal surfaces are parallel. The two flats 31 are adapted to receive corresponding flats 13 of the screw 1 and thus lock the latter against rotation after the insertion of the operating part 11 in the tubular part 25. In the direction toward the conical end part 29, the flats 31 are extended by longitudinal recesses 32 for receiving the operating part 11 of the screw 1. Lastly, in order to permit a visual checking of the position of the profiled end portion 12 on the flats 31, the tubular part 25 is provided with a transverse opening 33 in the region of the flats.

When the operating part 11 is inserted in the tubular part 25 with its end portion 12 locked against rotation between the flats 31, the surgeon slides the tube 27 along the tubular part 25 until the conical end portion 29 is made to grip round the operating part 11, the tapered portion 29 thus constituting a holding chuck for the screw 1. The two flats constitute additional means for preventing a reverse rotation of the pedicular screw 1 in the ancillary device 14. The ancillary device 14 also serves to screw the nut 23 clamping the screw 1 in the connection element 3. It is provided in its end 29 with a corresponding recess for engaging this nut 23.

The instrumentation just described is used in the following manner.

Before placing in position the support rods 2, which are for example the known Cotrel rods (Registered Trademark), the surgeon suitably anchors with his ancillary device 14 the double thread screws 1 in each of the pedicles of the vertebra L5 to correct. Then he secures the support rods 2 to the neighbouring vertebrae, or, as in the embodiment shown in FIG. 1, to the sacrum S and vertebra L4. Then he firmly fixes the connection elements 3 to the rods 2 by means of a radial clamping screw 20 (FIG. 1).

At this stage, the two transverse connection rods 5 are not yet installed. In order to correct the vertebra L5, i.e. to return it rearwardly (spondylolisthesis) and/or derotate it, the surgeon acts on the nuts 23 clamping the connection elements 3 by means of an ancillary device and preferably two ancillary devices, each being disposed on one of the nuts 23 of the two screws 1. He is now free to act, as desired, more on the screwing of one of the nuts 23 than on the screwing of the other, depending on the movement he wishes to impart to the vertebra L5, as he is free to act in an identical manner on the two nuts 23.

Each time the surgeon acts on one of the nuts 23, he exerts by the bearing of the screw thread-nut system on the connection element 3 firmly connected to the support rod 2, a traction on the vertebra L5 in a direction toward the connection element 3. When he acts on a single one of the nuts 23, he also produces a slight rotation of the vertebra L5 about itself. When he acts equally on both nuts 23, he produces a rearward return of the vertebra L5.

In all cases, the fine pitch of the screw thread 11 supporting the correction nut 23 permits acting very progressively on the vertebra. When the vertebra is finally in the position required by the surgeon, the latter severs the double thread screw 1 above the nut 23. The severing of the rod deforms the screw thread 11 and this subsequently prevents the unscrewing of the nut 23.

It is only at this moment that the transverse rods 5 interconnecting the rods 2 can be mounted, thereby achieving a rectangulation of the whole final instrumentation.

The instrumentation according to the invention is easier to place in position by the surgeon than that disclosed in said French patent 2 615 095, cheaper as concerns the fabrication of the screw, and more reliable in use; it no longer requires a transverse handling plate in the region of the connection elements 3. The screwing of the pedicular screws 1 by their profiled end portions 12 rather than by their central regions as in the aforementioned prior instrumentation, is also more convenient for the surgeon.

It must be understood that the scope of the invention is not intended to be limited to the described embodiments and various modifications may be made. For example, it is obvious that the end portion 12 may have any suitable profile other than that described, the same being true of the corresponding two flats 31 of the ancillary device 14.

Figure 6:
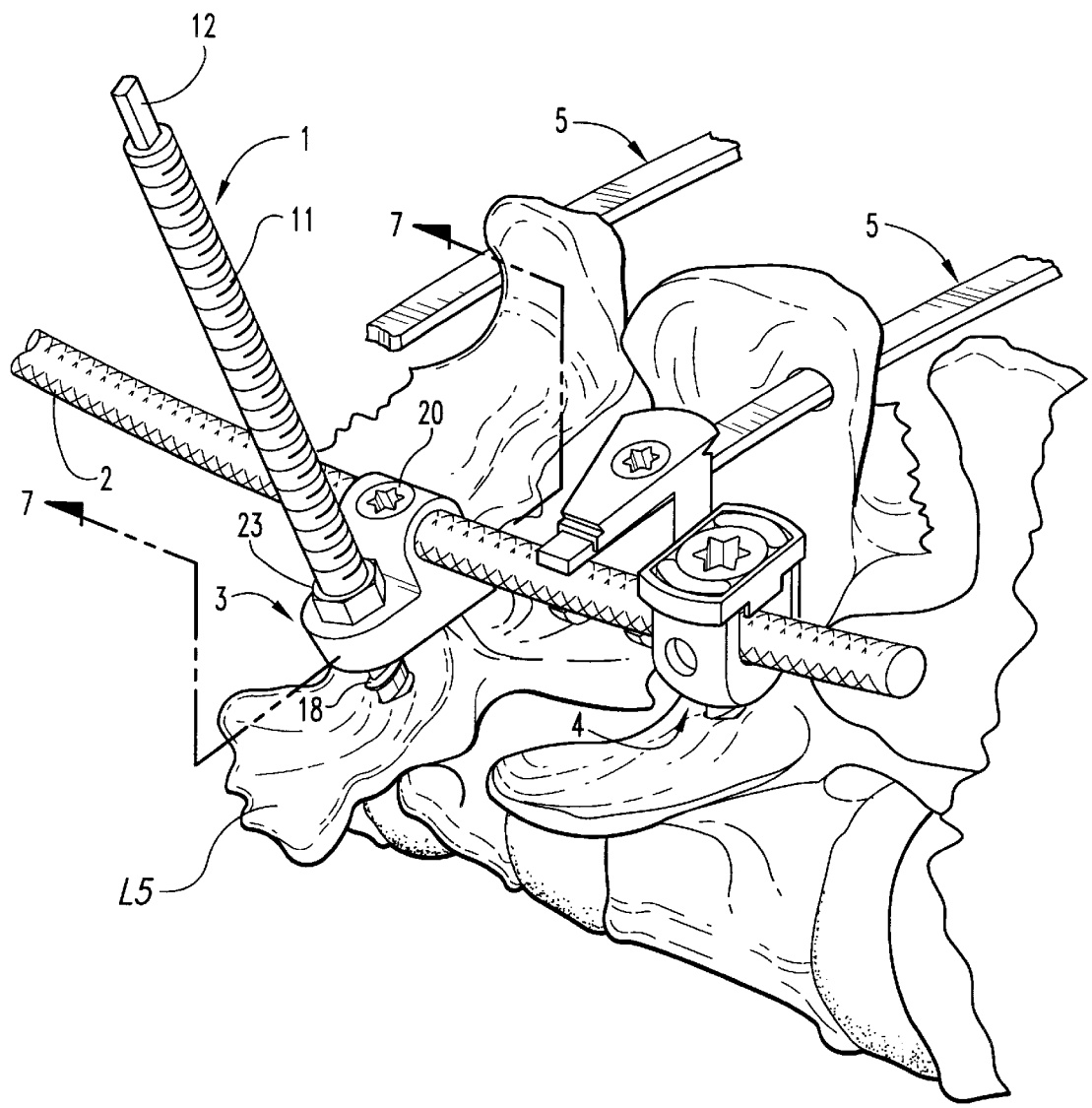
FIG. 6 is a perspective view to a larger scale of an alternative embodiment of the connection element between the osteosynthesis rod and the screw.

Likewise, in the alternative embodiment shown in FIG. 6, the connection element 3 may be constructed to have, as viewed in the transverse direction, a substantially L-shaped profile and be disposed in such manner that its planar surface 3c (in contact with the nut 23 in FIG. 3) is inverted, by turning the element round, so as to be closer to the adjacent vertebra.

What is claimed is:

1. A spinal fixation system, comprising:
    an elongated rod configured for attachment along a posterior aspect of a patient's spine, a set screw, and a nut;
    a pedicular screw having a first screw thread and a second screw thread, said first thread being configured for penetration into a posterior pedicular region of the patient's spine, said second thread being separated from said first thread by a bearing shoulder therebetween, said second thread being configured to extend outside the pedicular region when penetrated by said first thread;
    a connection element having a generally L-shaped profile defining a rod bore receiving said rod therethrough and a threaded bore intersecting said rod bore, said set screw being threaded into said threaded bore to correspondingly clamp said rod to said element, said element having two opposed planar surfaces defining an opening configured to receive said pedicular screw therethrough, said opening having a cylindrical central part extended at both ends by conical parts each opening out onto a respective one of said planar surfaces, said element bearing against said shoulder of said pedicular screw, said nut being threaded on said second thread of said pedicular screw fastening said pedicular screw to said element; and wherein said set screw is positioned anterior to said nut to provide a low profile construct when said rod and said pedicular screw are rigidly interconnected by said element.

2. The system according to claim 1, wherein said connection element is defined by a single unitary piece having a generally flat, planar posterior surface without protrusions.

3. The system according to claim 1, wherein said set screw is configured not to extend posterior to a generally flat, planar surface of said element when securely threaded into said threaded bore.

4. The system according to claim 1, wherein said cylindrical central part and said conical parts of said opening permit selection of an angular inclination of said pedicular screw through said opening from a range of about 30°.

5. The system according to claim 1, further comprising:

an ancillary device for screwing said pedicular screw by an operating part thereof, said operating part extending outside the pedicular region of penetration of said pedicular screw, said ancillary device including a rod provided with an end grip and a tubular end part which is arranged to permit the insertion therein of said operating part of said pedicular screw, said tubular end part having a conical free end portion remote from said grip an tapering in a direction toward said grip and defining at least one longitudinal slot, and a tube freely slidably mounted on said rod of said device configured for surrounding said conical free end portion of said tubular end part to grip said operating part of said pedicular screw.

* * * * *